United States Patent [19]

Imhof

[11] Patent Number: 5,538,725
[45] Date of Patent: Jul. 23, 1996

[54] METHOD OF INHIBITING METASTASIS BY ANTI-α6-INTEGRIN-ANTIBODIES

[75] Inventor: Beat A. Imhof, Basle, Switzerland

[73] Assignee: Hoffman-La Roche Inc., Nutley, N.J.

[21] Appl. No.: 289,598

[22] Filed: Aug. 12, 1994

Related U.S. Application Data

[63] Continuation of Ser. No. 117,903, Sep. 7, 1993, abandoned, which is a continuation of Ser. No. 959,016, Oct. 9, 1992, abandoned.

[30] Foreign Application Priority Data

Oct. 18, 1991 [EP] European Pat. Off. ............... 91810807

[51] Int. Cl.$^6$ .................................................. A61K 39/395
[52] U.S. Cl. .................................. 424/155.1; 424/156.1; 424/174.1
[58] Field of Search ............................... 424/130.1, 133.1, 424/134.1, 138.1, 141.1, 143.1, 144.1, 153.1, 154.1, 155.1, 156.1; 530/388.22, 387.7, 388.7, 388.73, 388.75, 388.8, 388.85

[56] References Cited

FOREIGN PATENT DOCUMENTS 478272  4/1992  European Pat. Off. .

OTHER PUBLICATIONS

Chatterjee et al Cancer Immunol Immunother 38:75–82 (1994).
Dermer Biotechnology 12: 320(1994).
Edgington Biotechnology 10: 383–389(1992).
Zetter Seminars in Cancer Biology 4:219–229 (1993).
Taylor Sher et al. Adv Cancer Res. 51: 361–390 (1988).
Hsi et al., "Monoclonal Antibody $GB_{36}$ Raised Against Human Trophoblast Recognizes a Novel Epithelial Antigen", Placenta 8:209–217 (1987).
Hogervorst et al., "Molecular Cloning of Human α6 Integrin Subunit", Eur. J. Biochem. 199:425–433 (1991).
Sonnenberg et al., "A Complex of Platelet glycoproteins Ic and IIa identified by a rat monoclonal antibody", J. Biol. Chem. 262:10376–10383 (1987).
Hemler et al., "Multiple very late antigen (VLA) heterodimers on platelets", J. Biol. Chem. 263:7660–7665 (1988).
Kennel et al., "Analysis of the tumor–associated antigen TSP–180", J. Biol. Chem. 264:15515–15521 (1989).
Kennel et al., "Analysis pf sirface proteins of mouse lung carcinomas using monoclonal antibodies", Cancer Res. 41:3465–3470 (1981).
Woodruff et al., "Specific cell–adhesion mechanisms determining migration pathways of recirculating lymphocytes", Annu. Rev. Immunol. 5:201–222 (1987).
Ruiz and Imhof," Embryonic colonization of the thymus by T Cell progenitors as a model for metastasis ", Metastasis: basic res. and its clinical applications, Rabes et al. (eds.) 44:318–331 (1992).

Imhof et al., "EA–1, a novel adhesion molecule involved in the homing of progenitor T lymphocytes to the thymus", J. Cell Biol. 114:1069–1078 (1991).
Ruiz et al., "Suppression of mouse melanoma metastasis by EA–1, a monoclonal antibody specific for α6 integrins", cell adhesion and communication, vol. 1, pp. 67–81 (1993).
Van Waes et al., "The A9 antigen associated with aggressive human squamous carcinoma is structurally and functionally similar to the new defined integrin $α^6β_4$", Cancer Res. 51:2395–2402 (1991).
Wieland et al., "Reversion of the transformed phenotype of B16 mouse melanoma: involvement of an 83 kd cell surface glycoprotein in specific growth inhibition", Cell 47:675–685 (1986).
Perotti et al., "Metastatic phenotype: growth factor dependence and integrin expression", Anticancer Research 10:1587–1598 (1990).
Ramos et al., "Analysis of integrin receptors for laminin and type IV collagen on tetastatic B16 melanoma cells", Cancer Research 50:728–734 (1990).
Koretz et al., "Expression of VLA–α2, VLA–α6 and VLA–β1 chains in normal mucosa and adenomas of the colon, and in the colon carcinomas and their liver metastases", American Journal of Pathology 138:741–750 (1991).
Harris et al., "Therapeutic antibodies–the coming of age", TIBTECH 11:42–44 (1991).
Tamura et al., "Epithelial Integrin $α_6β_4$: complete primary structure of $α_6$ and variant forms of $β_4$", J. Cell Biol. 111:1593–1604 (1990).
Hemler, "VLA proteins in the integrin family: structures, functions, and their role on leukocytes", 8:365–400 (1990).
Vollmers et al., "Monoclonal antibodies NORM–1, and NORM–2 induce more normal behavior of tumor cells in vitro and reduce tumor growth in vitro", Cell 40:547–557 (1985).
Kramer et al., "Melanoma cell adhesion to basement membrane mediated by integrin related complexes", Cancer Research 49:393–402 (1989).
Mortarini et al., "Heterogenity for integrin expression and cytokine mediated VLA modulationcan influence the adhesion of human melanoma cells to extracellular matrix proteins", Int. J. Cancer 47:551–559 (1991).
Vollmers, et al., FEBS 1542 172:17–20 (1984) "Monon-clonal antibodies which prevent experimental lung mestases".
Vollmers and Birchmeier, Proc. Natl. Acad. Sci. 80:6863–6867 (1983) "Monoclonal antibidies that prevent adhesion of B 16 melanoma . . . ".
Vollmers and Birchmeir, Proc. Natl. Acad. Sci. 80:3729–3733 (1983) "Monoclonal antibodies inhibit and adhesion of mouse B 16 . . . ".

*Primary Examiner*—Margaret Parr
*Assistant Examiner*—Phillip Gambel
*Attorney, Agent, or Firm*—George M. Gould; William H. Epstein; Catherine R. Roseman

[57] ABSTRACT

Polypeptides which bind to mammalian α6-integrin and inhibit metastasis.

3 Claims, 6 Drawing Sheets

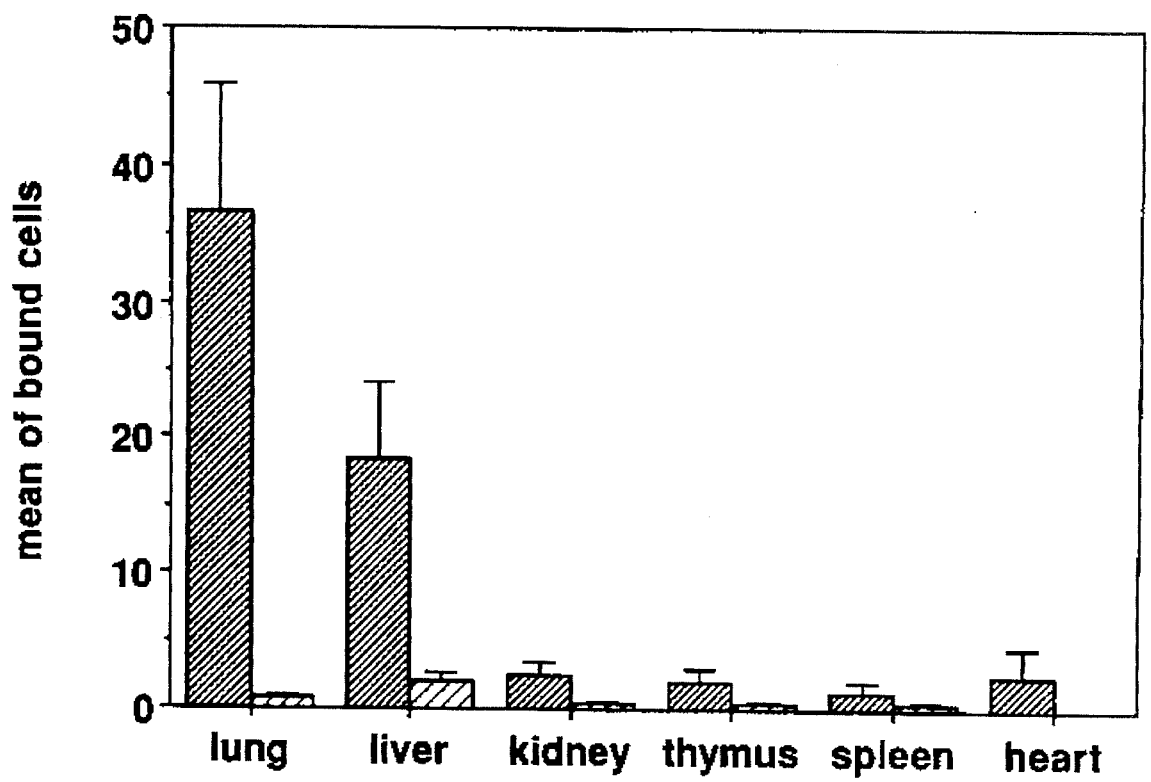
F I G. 1

FIG. 2b EA-1 LUNG
FIG. 2d EA-1 LIVER
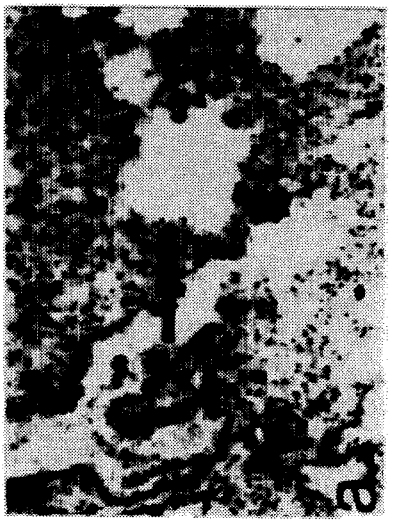
FIG. 2a CONTROL LUNG
FIG. 2c CONTROL LIVER ined metastasis that a further molecule,
METHOD OF INHIBITING METASTASIS BY ANTI-α6-INTEGRIN-ANTIBODIES This is a continuation, of application Ser. No. 08/117,903 filed Sep. 7, 1993 now abandoned, which is a continuation of application Ser. No. 07/959,016, filed Oct. 9, 1992, now abandoned.

BACKGROUND OF THE INVENTION

Adhesion of invasive cancer cells to vascular endothelium is a critical first and selective step in metastasis. During the last few years a large number of different adhesion molecules have been discovered to be involved in cell migration and homing mechanisms of hemopoietic cells. Transformed tumor cells can abuse such mechanisms in an uncontrolled way leading to metastasis in tissues other than those of their origin. The antigen known as α6-integrin is an adhesion molecule involved in metastasis.

Carcinoma, melanoma, and endothelial cells are known to adhere to laminin, an extracellular matrix molecule. Several integrin complexes, including α1/β1, α2/β1, and α6/β1 help mediate this binding. α6/β1 appears to react with laminin monospecifically.

Three antibodies directed against the α6 integrin chain have been described in the literature, each produced in a different manner. Antibody GoH3 was produced by immunizing rats with blood platelets and recognizes the platelet protein called complex Ic-IIa, which was subsequently defined as α6/β1 integrin. This antibody blocks cell-laminin interaction, and defines α6 integrin as a receptor for a fragment called E8 obtained by an elastase digest of laminin. [Sonnenberg et al., J. Biol. Chem. 262, 10376–10383 (1987); Hemler et al., J. Biol. Chem. 263, 7660–7665 (1988)]. Antibody 135-13C was prepared in rats against purified tumor associated proteins TSP-180, which is now described as α6/β4 integrin. This antibody has a less pronounced effect on cells binding to laminin. [Kennel et al., Cancer Res. 41, 3465–3470 (1981); Kennel et al., J. Biol. Chem. 264, 15515–15521 (1989)]. Finally, antibody GB36 was raised in mice against microvilli preparations of human placenta. The antibody recognizes cell surface proteins on human carcinoma cells [Hsi et al., Placenta, 8, 209–217 (1987)]. It was suggested in this reference that the protein (α6/β1 integrin) may play a role in maintenance of cell polarity, however no functional assays were performed.

Now it has been surprisingly found on the basis of the specific ability of the monoclonal antibodies of the present invention to inhibit metastasis that a further molecule, namely the antigen recognized by these monoclonal antibodies, which is known as α6-integrin [for a review see Hemler in Annu. Rev. Immunol. 8, 365–400 (1990)], is probably the most important endothelial adhesion molecule to be involved in metastasis.

The antibody of the present invention does not interfere with the binding of cells to laminin but blocks cell-cell interaction of melanoma cells with vascular endothelial cells. This finding strongly suggests that the antibody of the present invention recognizes a so far unknown binding domain on the α6 integrin chain-clearly different from the binding sites of GoH3, 135-13C or GB36, by the fact that GoH3 cross-reacts with skin homing lymphocytes in sheep whereas the antibody of the present invention does not.

SUMMARY OF THE INVENTION

The claimed invention is a monoclonal antibody or a functional derivative thereof which binds to mammalian α6-integrin, and which inhibits metastasis. The claimed antibody also prevents transformed cells from binding to endothelial cells.

BRIEF DESCRIPTION OF THE FIGURES

FIG. 1: In situ binding of B16 melanoma cells to mouse lung, liver, kidney, thymus, spleen and heart tissue. Filled bars (left): binding with control antibody; Hatched bars (right): binding with anti-β6i-mAbs.

FIG. 2: In situ binding of B16 melanoma cells to lung and liver sections.

FIG. 2a and 2b: Lung tissue incubated without (a) and with (b) anti-α6i-mAbs.

FIG. 2c and 2d: Liver tissue incubated without (c) and with (d) anti-α6i-mAbs.

DETAILED DESCRIPTION OF THE INVENTION

Figure 3:
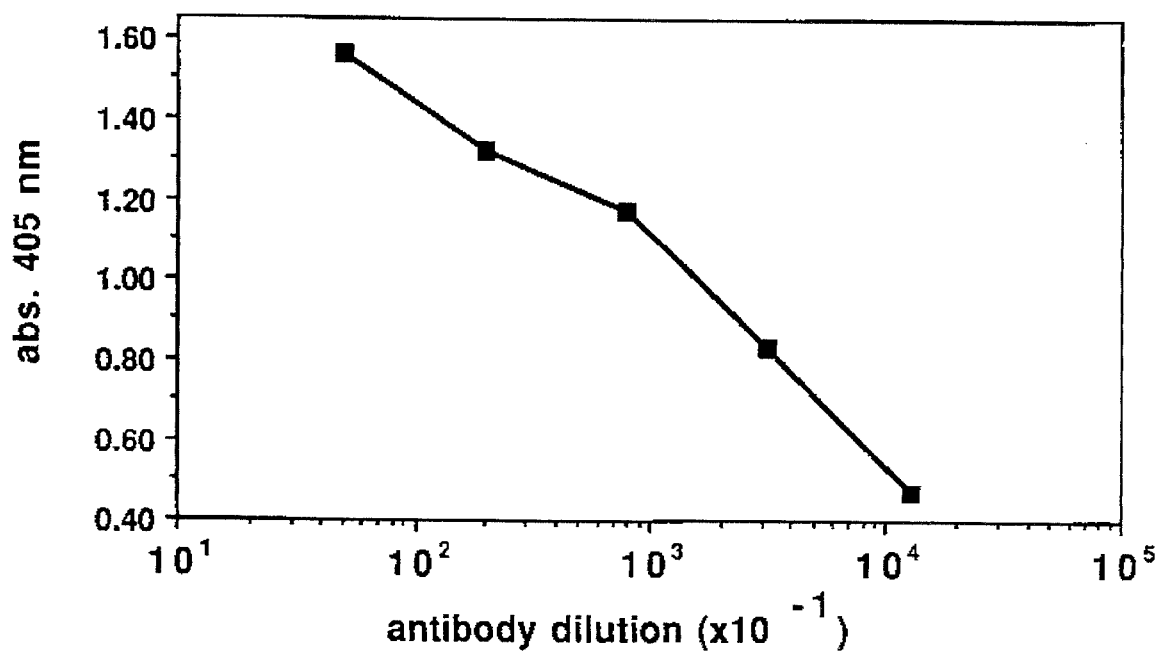
FIG. 3: Titration of anti-α6i-mAbs on human endothelial cells.

The claimed invention is a polypeptide which comprises a monoclonal antibody or a fragment thereof, which polypeptide is capable of binding to mammalian, preferably human, α6-integrin and of inhibiting metastasis in transformed cells. The polypeptide may in particular inhibit interaction between transformed cells and endothelial cells. Transformed cells include cells which carry α6-integrin or a ligand thereof as a surface molecule, such as melanomas, carcinomas, T-cell lymphomas, and sarcomas in particular melanomas. The polypeptide may be produced by conventional methods for synthesizing polypeptides and linking polypeptides. For example, the polypeptide may be produced by recombinant methods in a host cell into which has been inserted a nucleic acid sequence encoding the polypeptide, which sequence contains the sequence of the monoclonal antibody or fragment. The latter sequence may be obtained by sequencing the antibody using known methods. The polypeptide may be produced by chemically linking a selected peptide or peptides to the monoclonal antibody or a fragment using known methods to form covalent or other bonds between peptides and the antibody, or using known linker molecules to link peptides to the antibody.

It is also an object of the present invention to provide a monoclonal antibody, or a functional derivative thereof, or a fragment thereof, especially an Fab-fragment. Both the monoclonal antibody and the fragment are characterized by binding to mammalian, e.g. mouse or preferably human α6-integrin [anti-α6i-mAb] and by inhibiting metastasis of transformed cells, in particular by inhibiting the interaction of the transformed cells with the vascular endothelium. By transformed cells is meant those cells which are characterized by carrying α6-integrins as surface molecules, e.g. melanomas, carcinomas, T cell lymphomas or sarcomas, with melanomas and carcinomas, especially melanomas, and those cells which carry a ligand of α6-integrins as a surface molecule. A functional derivative of the claimed monoclonal antibody includes both fragments of the antibody, and larger molecular entities which incorporate the antibody o a fragment of the antibody, for example labelled antibody, or antibody combined with another molecule such as a toxin. Such derivatives may be produced by conventional methods.

It is also an object of the present invention to provide hybridoma cell lines secreting such monoclonal antibodies and the monoclonal antibodies secreted by such cell lines. Specifically, hybridoma cell lines secreting monoclonal antibodies binding to α6-integrin, preferably human α6-integrin, and inhibiting metastasis in transformed cells, in particular by inhibiting their interaction with endothelial cells. Transformed cells am as described above.

The hybridoma cell line "F3C34" obtained in accordance with the teaching of the present invention has been deposited on OCT. 17, 1991 at the Deutsche Sammlung von Mikroorganismen und Zellkulturen GmbH (DSM). F3C34 has the accession number ACC2023. It is furthermore an object of the present invention to provide such monoclonal antibodies or fragments thereof as therapeutic agents, especially for the treatment of cancer by the inhibition of metastasis.

Antibodies binding to α6-integrins can be prepared by using short peptides with amino acid sequences derived from the known amino acid sequence of human α6-integrin [Hogervorst et al., Eurp. J. Biochem. 199, 425–433 (1991)] as starting antigen. Such peptides can be prepared by methods of chemical peptide and protein synthesis known in the art, e.g. by partial or total liquid or solid phase synthesis as described e.g. by Gross and Meyenhofer in "The Peptides" Vols. 1–9, Academic Press, Inc., Harcourt Brace Jovanovich, Publs., San Diego (1979–1987) or by Fields and Nobel, Int. J. Pept. Prot. Res. 35, 161–214 (1990).

However, antibodies raised in such a way do not necessarily react with the native α6-integrins nor show the specific properties of those of the present invention. Therefore antibodies of the present invention can be prepared by conventional methods starting from α6-integrin positive cells, e.g. endothelial cells or transformed cells of endothelial origin, whereby an eEnd2-cell line is specifically preferred.

By injection of such an antigen into a non-human mammal, e.g. mouse, rabbit, rat or sheep, polyclonal antibodies can be obtained by methods known in the art from the serum of the mammal. Monoclonal antibodies can be prepared by known methods, for example, by recovering antibody-producing cells from such an immunized mammal and immortalizing said cells obtained in conventional fashion, such as fusion with myeloma cells e.g. PAI mouse myeloma cells, SP2/0- or SP2/0-Ag 14-cells [ATCC No. CRL 1581; ATCC No. CRL 8287] [for a general guideline for producing antibodies see e.g. "Antibodies—A Laboratory Manual" edt. by Harlow, E. and Lane, D., Cold Spring Harbor Laboratory, Cold Spring Harbor Laboratory Press, 1988] or as described in detail in Example I.

Supernatants of such hybridoma cultures have then to be screened for those secreting antibodies of the present invention by an assay determining the metastasis inhibiting properties of the antibodies of the present invention, e.g. an assay as described in detail in Example I. It is therefore also an object of the present invention to provide a process for the preparation of anti-α6i-mAbs and fragments thereof according to methods known in the art whereby hybridoma supernatants obtained are screened by the ability of the antibodies contained in such supernatants to inhibit metastasis and compounds obtained by such a process.

Anti-α6i-mAbs can be purified from hybridoma supernatants by conventional chromatographic procedures, for example, by ion-exchange-chromatography, affinity chromatography on protein G, using anti-immunoglobulin-antibodies or the antigen or a part thereof bound to a solid support, HPLC or the like.

For the production of large quantities of anti-α6i-mAbs in accordance with methods well-known in the art hybridomas secreting the desired antibody can be injected intraperitoneally into mice which have been pretreated with for example pristane before injection to produce ascites tumors in the mice. Up to around 100 mg of a monoclonal antibody can be produced by such ascites tumors in one mouse. Antibodies can be purified for example from ascites fluid produced by such tumors using methods described above.

Antibodies of the present invention can be characterized according to their subclass by known methods, such as Ouchterlony immunodiffusion. The antibody secreted by hybridoma cell line "F3C34" is of the igG2a subtype. Furthermore antibodies of the present invention can be characterized by their ability to inhibit metastasis of transformed cells, especially the interaction of the transformed cells with the vascular endothelium. Such activity can be determined by assays known in the art, e.g. in vitro by an assay such as described in Example I or in vivo by an assay such as described in Example II. Any transformed cell line carrying α6-integrin as a surface molecule, such as melanomas, e.g. B16 cells [Vollmers et al., Cell 40, 547–557 (1985)], carcinomas, e.g. KLN205 [ATCC CRL 1453] or CMT-93 [ATCC CCL 223] or MM45T [ATCC CRL 6420], T cell lymphomas, e.g. BW 5147 [ATCC TIB 48] or sarcomas, e.g. MM46T [ATCC CRL 6420] is useful in these assays. Useful in an in vitro assay is a suitable tissue material to which such cells and the antibodies of the present invention bind. An in vivo assay uses any type of animal in which such transformed cell lines lead to metastasis and to which the antibodies of the present invention crossreact. Metastasis can be determined by injecting such cells into the animal and detecting resulting migration and tumors. Mice are particularly useful in this regard. Inhibition of the interaction of such transformed cell lines with the vascular endothelium can be determined by assays known in the art, e.g. by an in vitro adhesion assay on monolayers of endothelial cells or cells of endothelial origin or as described in Example I. This is shown in FIG. 2 where arrows point to the position of the transformed cells binding to the vascular endothelium. Finally, antibodies of the present invention can be characterized by ability to block cell migration in an assay as described in Example V, or by failure to influence cell growth, in an assay as described in Example VI.

Furthermore antibodies of the present invention crossreact with human α6-integrin, as demonstrated by the detection of α6-integrin on the apical surface of human endothelial cells (see Example III) which correlates with in vivo staining of mouse α6-integrin on the apical surface of mouse blood vessel endothelium (see Example IV).

Anti-α6i-mAbs can be modified for various uses by methods known in the art or active fragments thereof can be generated as described for example in Example II. (Harlow & Lane s.a.). Fragments can be generated, by well-known methods for example, by enzymatic digestion of antibodies with papain, pepsin or the like. Specifically, papain cleavage of an antibody produces Fab fragments. Pepsin cleavage can be used to produce an F(ab)$_2$ fragment. In addition the antibodies of the present invention can be modified, for example by the addition of a polyethyleneglycol subunit as known in the art and described in U.S. Pat. No. 4,179,337, or coupled, for example, to a fluorescent dye, a colour-producing substance such as an enzyme [enzyme linked immunosorbent assay (ELISA)] or a radioactive substance [radioimmunoassay (RIA)] in accordance with methods well-known in the art and used in such assay systems as known in the art. Furthermore such antibodies can be "humanized" according to methods known in the art, and disclosed in the case of an antibody specific for a subunit of the human interleukin 2 receptor in International Patent Application Publication No. WO 90/7861. Accordingly functional derivatives as described above are also an object of the present invention.

Monoclonal antibodies of the present invention may be used as therapeutic agents, especially in the treatment of cancer e.g. by inhibiting metastasis especially in the case of secondary metastasis during surgery. The antibodies can be used, if desired, in combination with other pharmaceutically active substances, preferably monoclonal antibodies or peptides against different adhesion molecules present on vascular endothelium or the metastatic cell, with conventionally used pharmaceutically acceptable solid or liquid carrier materials. Dosage and dose rates may be chosen by analogy to dosage and dose rates of currently used antibodies in clinical treatment of various diseases.

Accordingly it is also an object of the present invention to provide anti-α6i-mAbs which can be clinically used. Furthermore it is an object of the present invention to provide a pharmaceutical composition which contains one or more anti-α6i-mAbs or fragments thereof, if desired, in combination with additional pharmaceutically active substances and/or non-toxic, inert, therapeutically compatible carrier materials. The preparation of such pharmaceutical compositions can be achieved in accordance with methodology known to one skilled in the art.

Furthermore monoclonal antibodies of the present invention can be used as a marker in the diagnosis of illnesses, especially cancer. It is well known in the art that for such purposes monoclonal antibodies can be coupled, for example, to a fluorescent dye, a colour producing substance such as enzyme [enzyme linked immunosorbent assay (ELISA)] or a radioactive substance [radioimmunoassay (RIA)] in accordance with methods well-known in the art and used in such conventional assay systems as described, e.g. in Harlow & Lane (s.a.).

The following Examples are provided to illustrate the invention without limiting it.

EXAMPLE I

Preparation of anti-α6i-mAbs

Confluent endothelial cells (eEnd2-cell line) from a 150 cm$^2$ culture flask were irradiated with 10,000 rad and harvested with cell scrapers (Costar Data Packaging). These cells were then washed with Dulbecco's phosphate buffered saline (DPBS) (Gibco BRL), mixed 1:1 with complete Freund's adjuvant for a final volume of 300 µl, and injected subcutaneously into the dorsal surface of the hind foot of a 2-mouth-old PVG rat [BRL, Füllinsdorf, CH]. Injections with cells in DPBS only were repeated after 7 and 14 days. At day 17, the draining popliteal lymph node was dissected from the rat. The tissue was enzymatically digested using the following enzyme stock solutions: 150 mg/ml protease type IX (P-6141; Sigma Chemical Co., Buchs, CH); 8 mg/ml collagenase CLS 4 (Worthington Biochemical Corp., Freehold, N.J., USA); 10 mg/ml DNAse I (Sigma Chemical Co.). The enzyme solutions were mixed to a final volume of 2 ml (0.5 ml collagenase, 0.1 ml protease, 0.1 ml DNAse, 1.3 ml IMDM [Iscove's modified MEM; Gibco BRL, Gaithersburg, Md., USA]. A lymph node was opened by two slight crosscuts using a 25-gauge needle. Stroma were then digested at 37° C. for two 30-min periods each with 1 ml enzyme cocktail. The cells were then carefully released into IMDM with Pasteur pipettes, washed in 50 ml IMDM, and counted. One part lymph node cells was then mixed with five parts mouse Sp2/0 myeloma cells [ATCC CRL 1581], centrifuged, and fused with PEG 4000 (E. Merck, Darmstadt, FRG) as described in Harlow and Lane (1988). The cells were then plated (100 µl) into conditioned medium in microtiter plates (96 wells; Costar Data Packaging) at a density of 5×10$^4$ cells/well in IMDM selection medium containing HAT (Gibco BRL), 10% fetal calf serum (FCS) (Boehringer Mannheim GmbH, Mannheim, FRG), 50 mM b-mercaptoethanol, penicillin/streptomycin, and glutamine. Conditioned medium was produced by culturing 10$^4$ PVG rat thymocytes (100 µl/well) in selection medium for three days before fusion.

Screening of hybridoma supernatants for metastasis inhibiting mAbs was based on blocking of B16/129 melanoma cell binding to frozen sections of mouse lung or liver tissue.

In situ binding was performed on freshly prepared frozen sections from adult mouse tissue [Woodruff et al., Annu. Rev. Immunol. 5, 201–222 (1987)]. Organs were embedded and frozen in Tissue-Tek, O.C.T. Compound (Miles Inc., Elkhart, Ind., USA), sectioned to 5 µm thickness, and mounted onto glass slides. The sections were outlined by a PapPen (SCI Science Services, Munich, FRG) and immediately placed into DPBS containing 1% bovine serum albumin (BSA) for at least 10 min. Slides were dried around the PapPen marked area and the tissue section then loaded with 10$^5$ B16 melanoma cells in 200 ml DPBS containing 20% hybridoma supernatant of cultures prepared as described above or control antibody (rat IgG from Jackson Immuno Research Lab). Binding was allowed to occur for 40 min at 8° C. on a mini-shaker (Kühner, Basel, CH) at 50 rpm. Slides were then placed vertically into DPBS containing 0.5% glutaraldehyde and 2% formaldehyde, where non-bound cells were allowed to fall off. After 20 min. of fixation at room temperature and counterstaining in 0.25% thionine-acetate in 20% ethanol, B16 cells bound to the tissue section under study were counted using a Zeiss Axiophot light microscope. Results are given in FIG. 1 with respect to lung and liver tissue sections and additional tissue sections (kidney, thymus, spleen and heart) prepared in the same way as described above for lung and liver whereby left colums give mean values of bound B16 cell to tissues as indicated in the absence of anti-α6i-mAbs and right columns in the presence of anti-α6i-mAB containing hybridoma supernatants. FIG. 2 shows lung tissue sections incubated with control supernatants (a) or anti-α6i-mAb containing hybridoma supernatants (b) and liver tissue sections incubated with control supernatants (c) or anti-α6i-mAb containing hybridoma supernatants (d).

Immunoprecipitation with antibodies prepared as described above and partial N-terminal sequencing of the precipitated antigen showed that the antibody is directed to mouse α6 integrin since the first 15 amino acids sequenced are, with the exception of position 14 (serine instead of tyrosine) identical to the sequence of human α6 integrin.

EXAMPLE II

In vivo characterisation of anti-α6i-mAbs

Thawed B16-129 cells [Vollmers et al. (1985)], a subline from B16-F10 mouse melanoma cells (passage 3) were passaged maximally 2–3 times in DMEM (Gibco, BRL, Paisley, UK) containing 10% fetal calf serum (FCS) (Boehringer Mannheim GmbH, Mannheim, FRG) quickly trypsinized, washed with complete medium and resuspended in PBS. Intraveneous injection of $1.5 \times 10^5$ cells resulted in 300–500 lesions per lung after 10 days, injection of $7.5 \times 10^4$ resulted in 30–50.

For characterisation of anti-α6i-mAbs in vivo B16-129 cells were injected i.v. into mice together with control rat-mAb or anti-α6i-mAbs or Fab fragments thereof. Lung B16-129 colonies were counted after 10 days. Results are given in Tables I and II.

With respect to Table I ten mice per group were injected with $7.5 \times 10^4$ cells each. With respect to Table II mice were injected with $1.5 \times 10^5$ B16-129 cells: (a) injection of cells was made simultaneously with the antibodies, (b) antibodies were injected 24 hours before the cells and (c) melanoma cells were incubated 60 min. with antibodies, washed and then injected into animals. The table represents one out of three experiments performed, 5 mice were injected per group.

TABLE I

|  | Control | 500 μg anti-α6i-mAb/mouse | 250 μg Fab of anti-α6i-mAb/mouse | 500 μg Fab of anti-α6i-mAb/mouse |
| --- | --- | --- | --- | --- |
| Lung lesions per mouse | 37 (5–113) | 1 (0–4) | 0 | 0 |

TABLE II

| Type of treatment | Control | Fab of anti-α6i-mAb | Reduction of lung lesions |
| --- | --- | --- | --- |
| Simultaneous injection (a) | 610 (321–993) | 147 (3–481) | 86% |
| Pretreatment of mice (b) | 742 (321–1025) | 474 (45–1008) | 36% |
| Pretreatment of B16-129 melanoma (c) | 465 (208–563) | 224 (145–253) | 62% |

Anti-α6i-mAbs were purified from hybridoma supernatant using protein G affinity columns (Pharmacia, Uppsala, Sweden). Fab fragments thereof were prepared using the kit "AvidChrom" (BioProbe International, Tustin, Calif., USA). As control normal rat IgG (Jackson Immuno Research Laboratories, West Grove, Pa., USA) was used.

Example III

Binding of anti-α6i-mAbS to human endothelial cells

Binding of anti-α6i-mAbs on the apical surface of human endothelial cells was shown in the following manner: HUV-EC-C-cells [ATCC CRL 1730] were grown to confluency using methods known in the art, stabilized by formaldehyde fixation, and incubated with a graded dilution of a 100 μg/ml stock solution of anti-α6i-mAbs. Surface bound antibody was detected by biotinylated mouse anti-rat antibody (Jackson Immuno Research, West Grove, Pa., USA) followed by streptavidin coupled to peroxidase and 2,2'-Azino-bis(3-ethylbenzthiazoline-6 -sulfonic acid), ABTS (Sigma), as a substrate readable at 405 nm. Results are shown in FIG. 3.

EXAMPLE IV

Figure 4B:
FIG. 4: Vascular surface staining in vivo. Panels 4a and 4b are phase contrast and immunofluorescence micrographs of lung from a mouse injected with anti-α6i-mAbs.
FIGS. 4c and 4d are phase contrast and immunofluorescence micrographs of liver from mouse injected with anti-α6i-mAbs.
Figure 4D:
Figure 4A:
Figure 4C:
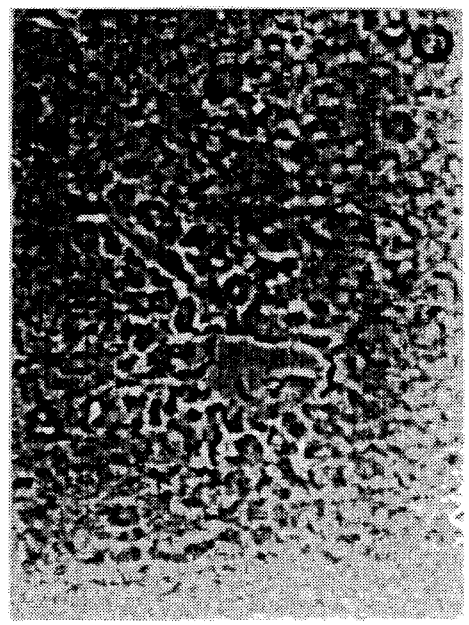

Vascular surface staining in vivo 1 mg of protein G-SEPHAROSE purified anti-a6i-mAbs was injected into the tail vein of C57BI/6 mice [IFFAC-CREDO, Lyon, F]. Animals were sacrificed 4 hrs after injection, the tissues embedded in Tissue-Tek (Miles Inc, Elkart, Id. 46515, USA) sectioned on a cryostat and prepared for immunofluorescence staining using FITC conjugated goat anti-rat IgG antibody (Jackson Immuno Research, West Grove, Pa., USA). FIG. 4(a) shows a phase contrast image and FIG. 4(b) an immunofluorescence staining of lung. FIG. 4(c) shows a phase contrast image and FIG. 4(d) shows a immunofluorescence stain of liver. Injection of 1 mg rat IgG as a control showed no signal.

Example V

Blocking of cell migration

Figure 5A:
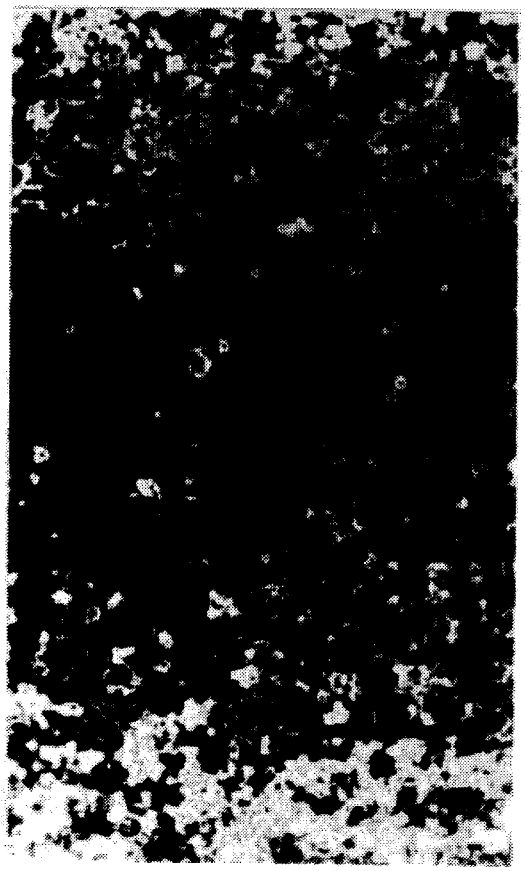
FIG. 5: Blocking of cell migration. Migration of B16-129 melanoma cells in 0.3% serum without anti-α6i-mAbs 5a and with anti-α6i-mAbs 5b.
Figure 5B:
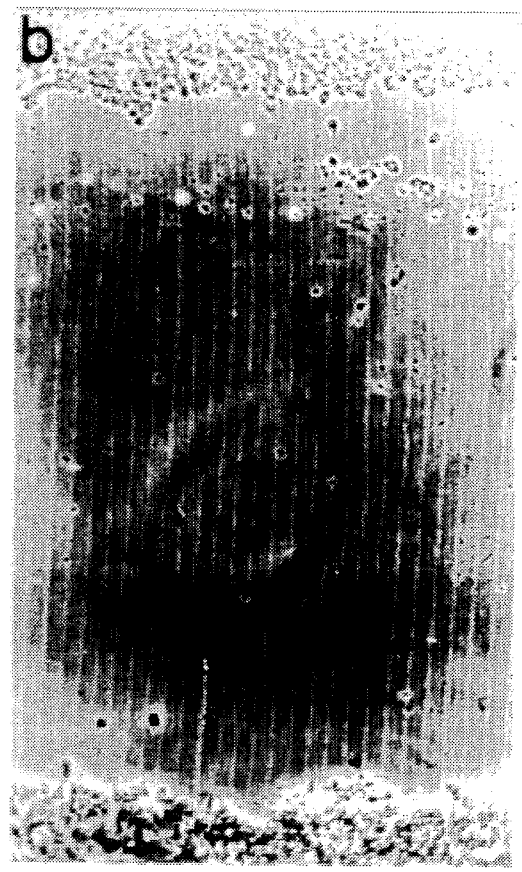

B16-129 melanoma cells were plated to confluency in 12 well culture cluster dishes (Costar) in medium containing 0.3, 3 or 10% fetal calf serum. The monolayer was then wounded by scratching the dish using blue pipette tips (Gibco BRL, Gaithersburg Md., USA), this left a sharply separated region without cells. Cell migration into this region was subsequently observed after further 24 hours culturing. There was no influence on cell migration when the cells were grown in either 3 or 10% serum (not shown), however in 0.3% serum anti-ec6imAb blocked B16-129 cell migration dramatically. FIG. 5(a) shows the migration of cells in 0.3% serum towards the center of the wounded region in the presence of 30 g/ml control rat IgG and (b)in 30 μg/ml anti-α6i-mAb.

EXAMPLE VI

Influence on cell growth

Figure 6:
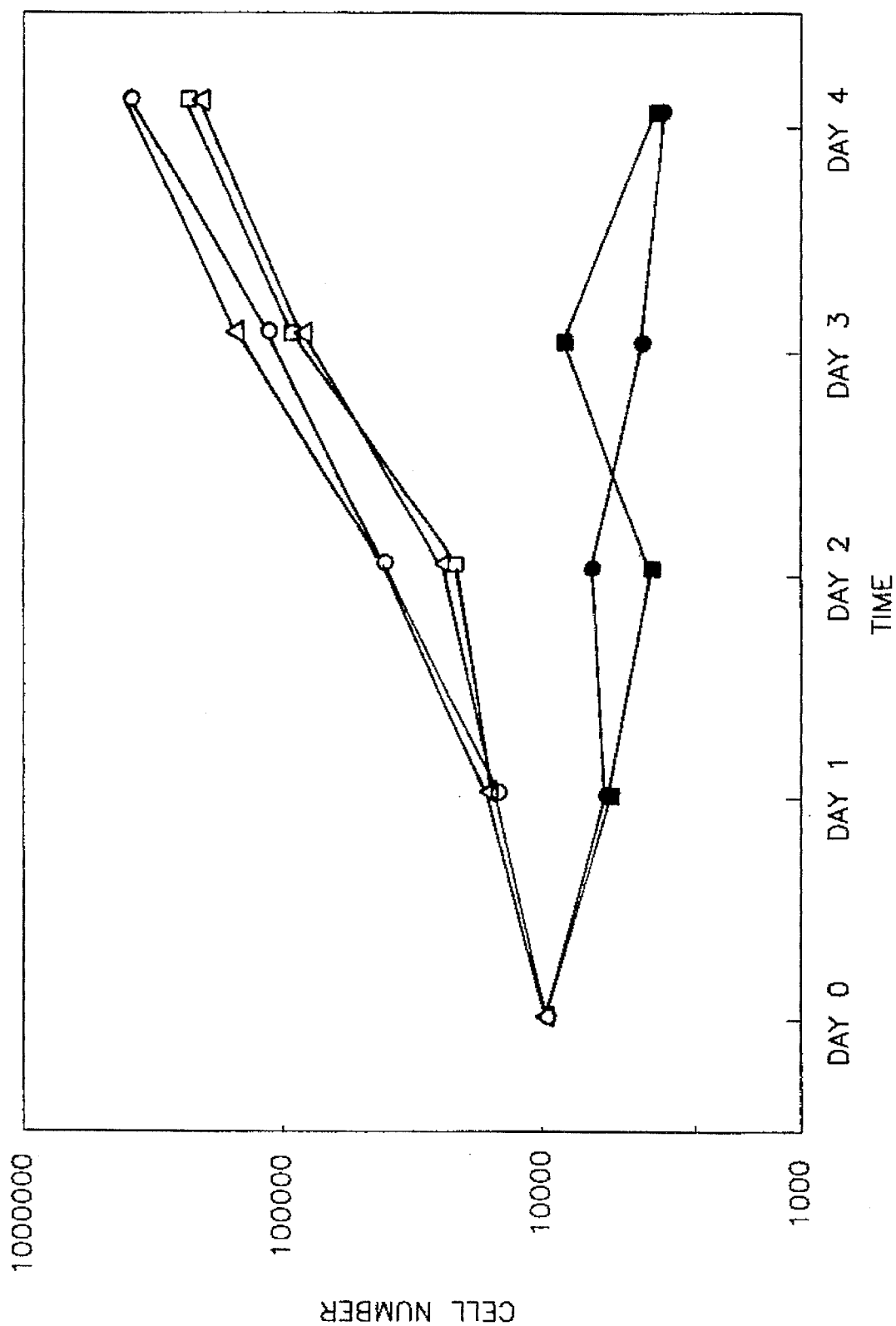
FIG. 6: Influence on cell growth. B16-129 melanoma cells in 0.3%, 3.0%, or 10.0% FCS with or without anti-α6i-mAbs. Filled boxes: 0.3% FCS and control mAb; Filled circles 0.3% FCS and anti-α6i-mAbs; open squares: 3.0% FCS and control mAb; open triangle: 3.0% FCS and anti-α6i-mAb; Filled triangle: 10.0% and control mAb; Open circle: 10.0% FCS and anti-α6i-mAb.

B16-129 melanoma cells were plated in 24 well culture cluster dishes (3524, Costar, Cambridge, Mass., USA) at a density of $10^4$ cells per well in medium containing either 0.3, 3 or 10% fetal calf serum in the presence of 30 μg/ml anti-α6i-mAb (A) or as a control in the presence of 30 μg/ml of a rat IgG-mAb (B). Over 4 days the cells from two wells per condition were trypsinized and counted. The cells grew readily in 10 and 3% serum but they were quiescent in 0.3% serum over the 4 days tested. Under neither of these conditions anti-α6imAb had any effect on cell growth. Results are given in FIG. 6 wherein filled boxes refer to 0.3% of fetal calf serum and (B), filled circles refer to 0.3% and (A), open boxes refer to 3% of serum and (B), open triangles refer to 3% serum and (A), filled triangles refer to 10% of serum and (B) and open circles refer to 10% of serum and (A).

I claim:

1. A method of inhibiting metastasis by transformed cells of mammals having surface α6 integrin molecules which comprises administering to said transformed cells a monoclonal antibody or antigen binding fragment thereof which binds specifically to mammalian α6-integrin and does not bind to laminin or reduce melanoma cell growth, and which inhibits B16 melanoma cells from binding to lung tissue thereby inhibiting said metastasis.

2. A method of claim 1 wherein the antigen binding fragment is an Fab fragment.

3. A method of claim 1 wherein the transformed cells are selected from the group consisting of melanoma, carcinoma, sarcoma and T-cell lymphoma cells.

* * * * *